United States Patent
Das et al.

(10) Patent No.: US 10,953,445 B2
(45) Date of Patent: Mar. 23, 2021

(54) SINGLE PROCEDURE INDICATORS

(71) Applicant: Greatbatch Ltd., Clarence, NY (US)

(72) Inventors: Biswa P. Das, Tonawanda, NY (US); Ashish Shah, East Amherst, NY (US)

(73) Assignee: VIANT AS&O HOLDINGS LLC, Foxborough, MA (US)

( * ) Notice: Subject to any disclaimer, the term of this patent is extended or adjusted under 35 U.S.C. 154(b) by 343 days.

(21) Appl. No.: 15/790,100

(22) Filed: Oct. 23, 2017

(65) Prior Publication Data

US 2018/0111177 A1 Apr. 26, 2018

Related U.S. Application Data

(60) Provisional application No. 62/411,005, filed on Oct. 21, 2016.

(51) Int. Cl.
| | |
|---|---|
| *G09F 3/00* | (2006.01) |
| *A61L 31/14* | (2006.01) |
| *A61L 31/02* | (2006.01) |
| *A61L 31/04* | (2006.01) |
| *B09B 3/00* | (2006.01) |
| *C08L 33/02* | (2006.01) |
| *C08K 3/34* | (2006.01) |
| *C08K 3/26* | (2006.01) |

(52) U.S. Cl.
CPC ......... *B09B 3/0075* (2013.01); *A61L 31/028* (2013.01); *A61L 31/041* (2013.01); *A61L 31/048* (2013.01); *A61L 31/14* (2013.01); *G09F 3/0291* (2013.01); *C08K 3/26* (2013.01); *C08K 3/34* (2013.01); *C08K 3/346* (2013.01); *C08K 2003/265* (2013.01); *C08L 33/02* (2013.01); *C08L 2203/02* (2013.01)

(58) Field of Classification Search
None
See application file for complete search history.

(56) References Cited

U.S. PATENT DOCUMENTS

| | | | |
|---|---|---|---|
| 7,811,530 B2 | 10/2010 | Morrison et al. | |
| 2002/0150761 A1* | 10/2002 | Lange | A61L 15/28 428/407 |
| 2009/0047176 A1* | 2/2009 | Cregger | A61L 2/28 422/28 |
| 2010/0322996 A1* | 12/2010 | Wibaux | C09J 9/00 424/443 |
| 2014/0200580 A1* | 7/2014 | Joseph | A61L 2/16 606/45 |
| 2015/0209200 A1* | 7/2015 | Fouillet | A61L 15/60 604/369 |

(Continued)

OTHER PUBLICATIONS

ECA Medical Instruments Disposable Fixation Kit Used in First Surgery to Secure Intelligent Implant Systems Revolution Spine Implant. Business Wire, A Berkshire Hathaway Company.

(Continued)

*Primary Examiner* — Jill A Warden
*Assistant Examiner* — Brittany I Fisher
(74) *Attorney, Agent, or Firm* — Steven J. Grossman; Grossman, Tucker, Perreault & Pfelger PLLC

(57) ABSTRACT

Disclosed herein are single use indicators and methods for employing the same. Such indicators and their uses are directed towards identifying the discharge status of single procedure devices, which are typically, but not limited to, medical devices.

11 Claims, 2 Drawing Sheets

(56) References Cited

U.S. PATENT DOCUMENTS

| | | |
|---|---|---|
| 2016/0022853 A1 | 1/2016 | Hajime et al. |
| 2016/0161919 A1* | 6/2016 | Patel .................... G01N 31/229 |
| | | 73/1.42 |
| 2016/0187309 A1 | 6/2016 | Kang et al. |
| 2017/0007852 A1* | 1/2017 | Isola .............. A61B 17/320068 |

OTHER PUBLICATIONS

World Health Organization, Patient Safety Health care-associated infections Fact Sheet.

* cited by examiner

SINGLE PROCEDURE INDICATORS

CROSS-REFERENCE TO RELATED APPLICATIONS

This application claims priority to U.S. Provisional Application No. 62/411,005 "Water Absorbing Polymer As Single Use Indicator For Single Process Reamers," which was filed on Oct. 21, 2016, the entire contents of which are hereby incorporated by reference in their entirety.

FIELD OF THE INVENTION

The present disclosure relates generally to single use indicators. In particular, the present technology concerns such indicators and their use in identifying the discharge status of single procedure devices, which are typically, but not limited to, medical devices.

BACKGROUND OF THE INVENTION

The following description is provided to assist the understanding of the reader. None of the information provided or references cited is admitted to be prior art.

On a global scale, health care-associated infections, i.e., nosocomial infections, impact hundreds of millions of patients annually, which consequently imparts a considerable mortality rate. To this end, of every one-hundred hospitalized patients at any given time, seven in developed countries, and ten in developing countries, will acquire at least one nosocomial infection. See World Health Organization Patient Safety, "Health Care-Associated Infections: Fact Sheet," 2011.

Albeit endemic to all health care environments, nosocomial infections are nevertheless markedly higher in low and middle-income countries compared to higher income nations, and more specifically in neonatal patients and those requiring intensive care. See id. And, while urinary tract infection is the most frequent health care-associated infection in high-income countries, surgical site infection is the leading infection in settings with limited resources, affecting up to one-third of operated patients in those countries. Notwithstanding the demographic character of these hospital acquired afflictions, nosocomial illnesses beget a substantial economic burden that requires further attention.

Accordingly, there has been a gradual shift in recent years from reusable instruments that potentially harbor infectious pathogens, i.e., to the extent that sterilization procedures break-down or are inadequate, to single procedure medical instruments which theoretically possess a decreased risk of transmitting nosocomial pathogens. The potential for reuse of single procedure devices, however, cannot be ignored. Whether by mistake, misuse, or reprocessing, circumstances remain in which single procedure devices are employed beyond their intended lifecycle.

To a large extent, such hazardous recycling of single procedure devices would be curtailed by implementing a system in which one or more single-use indications conspicuously identify when a device is at its end-of-use. By possessing a distinct indication—that a single procedure device has been discharged—the risk of mistakenly recirculating such a device back into the operating room can be greatly reduced. Hence, there is a current need to address the foregoing issues by developing low cost, biocompatible, single-use medical device indicators that are readily ascertainable to health care personnel. See, e.g., Schultz, J. B., "Disposables in the O.R. 'Cover Story: Disposables, ECA Medical Instruments,'" (2013).

SUMMARY

In one aspect, the present disclosure provides a method for determining the discharge status of a single procedure device, including (a) providing the device, where the device includes at least one indicator region configured to transition from an unmodified state to a modified state in response to an exposure; (b) subjecting the device to the exposure after the single procedure has been performed using the device; (c) assessing the transition state of the at least one indicator region, where the modified state of the at least one indicator region irreversibly identifies that the device has been subjected to the exposure after the single procedure; and (d) determining the discharge status of the device based on the transition state assessment of the at least one indicator region, where the device is affirmatively discharged when the at least one indicator region is in the modified state.

In some embodiments, the at least one indicator region includes a biocompatible composition entailing one or more of (i) at least one filler, (ii) one or more binders, (iii) one or more additives, and (iv) a solvent, and combinations thereof. In illustrative embodiments, the methods further entail one or more of (e) labelling the affirmatively discharged device as end-of-use, (f) segregating the affirmatively discharged device from other single procedure devices that have not been affirmatively discharged, and (e) disposing of the affirmatively discharged device.

In some embodiments, the exposure entails contacting the device including the at least one indicator region with water, where the water contact occurs via one or more autoclave cycles, steam sterilization cycles, sterilization procedures, simple application of water and/or steam, aqueous disinfection, washing, and/or the sterile application of water or steam. In some embodiments, the exposure is one or more autoclave steam sterilization cycles. In some embodiments, the exposure comprises subjecting the device including the at least one indicator region to one or more steam sterilization cycles. In suitable embodiments, the one or more steam sterilization cycles are performed for a duration at temperatures and pressures sufficient to (i) transition the at least indicator region from the unmodified state to the modified state, and (ii) sterilize the device.

In some embodiments, the device is a medical device, where the medical device is a single use orthopedic surgical device in some embodiments. The medical device is selected from, in certain embodiments, reamers, awls, rod benders, drill guides, guide tubes, distance gages, inserters, implant holders, clamps, portals, screwdrivers, spacers, distracters, plate benders, broaches, fusion plates, fusion screws, spinal rods, spinal connectors, artificial discs, tissue-anchoring devices, fixation devices, Stineman pins, dilators, joint spreaders, rasps, fusion cages, Kerrisons and Rongeurs, and combinations thereof. In some embodiments, the medical device has a proximal end and a distal end, where the at least one indicator region is located at or about the proximal end of the medical device.

In suitable embodiments, the at least one indicator region has a biocompatible composition including at least one filler and one or more binders, where the at least one filler is one or more superabsorbent polymers possessing a swelling capacity range of about 30-500 fold the volume of the one or more superabsorbent polymers prior to being subjected to the exposure. In illustrative embodiments, the one or more superabsorbent polymers are selected from polyacrylates, polyacrylamides, polyacrylamide copolymers, polyacrylic acid, sodium polyacrylate, potassium polyacrylate, lithium polyacrylate, ammonium polyacrylate, ethylene maleic anhydride copolymer, carboxymethylcellulose, polyvinyl alcohol copolymers, polyethylene oxide, and copolymers of polyacrylonitrile, and combinations thereof.

In illustrative embodiments, the biocompatible composition is formulated such that after the biocompatible composition is applied to a proximal end of a device, i.e., constituting the indicator region, the superabsorbent polymer (SAP) is sterically arrange throughout the indicator region to ensure that water, when present, is able to contact—and accordingly swell—the SAP, i.e., the water is accessible to the SAP for adsorption via SAP surface exposure. Likewise, in some embodiments of the present invention, the SAP molecules are contiguously conformed or are arranged in a substantially contiguous configuration within the biocompatible composition, and consequently throughout the indicator region, such that water, when present, is able to continuously percolate the indicator region until the SAP swelling capacity is achieved.

The one or more binders of the present technology, in some embodiments, are selected from alkyds, acrylics, vinyl-acrylics, polyurethanes, polyesters, melamine, epoxies, silanes, siloxanes, and oils, and combinations thereof. In illustrative embodiments, the methods further include one or more solvents, additives, accelerants, surfactants, emulsifiers, reducing agents, fluidizing agents, detergents, wetting agents, and dispersants, and combinations thereof. The one or more additives, moreover, are selected from clays, kaolin, kaolinite, halloysite, diaspore, bentonite (Fuller's earth), ball clay, common clay, shale, fire clay, illite, chlorite, smectite minerals, quartz, limestone, silicate compounds, and quartz, and combinations thereof, in certain embodiments.

In some embodiments, the one or more solvents are selected from one or more of non-polar solvents, polar solvents, non-aqueous solvents, aqueous solvents, protic solvents, aprotic solvents, lipophilic solvents, hydrophilic solvents, water-miscible solvents, and water-immiscible solvents, and combinations thereof. In illustrative embodiments, the one or more binders are dissolved in the one or more solvents. In some embodiments, the one or more fillers, polymers and/or superabsorbent polymers (SAPs) are not miscible in the solvent. In suitable embodiments, the one or more solvents are selected from xylene, toluene, alcohols, and ketones, and combinations thereof.

In illustrative embodiments, the at least one filler is present at a range of about 30-90 by weight percentage in the biocompatible composition, while the one or more binders are present at a range of about 10-70 by weight percentage in the biocompatible composition. Likewise, the one or more additives are present at a range of about 0.1-10 by weight percentage in the biocompatible composition in some embodiments, where the one or more solvents are present at a range of about 0.1-60 by weight percentage in the biocompatible composition in suitable embodiments. In some embodiments, the at least one indicator region is permanently affixed to the device. In other embodiments, the biocompatible composition of the indicator is a material component of the device itself, e.g., the materials that constitute the device are composed of, inter alia, the biocompatible composition of the indicator.

In illustrative embodiments, the at least one indicator region is permanently adhered to the device as one or more coated layers or as an independently affixed layer by a surface application process selected from coating, painting, encapsulation, dip coated, chemical adsorption, immobilization, piezoelectric printing, thermal printing, coated rolling, roll-to-roll conveying, spray nozzle application, electroactive deposition, chemical vapor deposition, magnetoactive deposition, laser induction, and imprinting, and any combination thereof. In some embodiments, the biocompatible composition of the indicator is a material component of the device itself, e.g., the materials that constitute the device are composed of, inter alia, the biocompatible composition of the indicator.

In illustrative embodiments, the at least one indicator region is present as a surface layer on the device, where the thickness of the surface layer is about 100 µm to 3 mm. In certain embodiments, the irreversible identification is a visual and tactile identification. In some embodiments, the modified state of the at least one indicator region renders the device clinically impractical for reuse. In certain embodiments the one or more superabsorbent polymers is sodium polyacrylate, where the sodium polyacrylate possesses a degree of ionization ranging from about 30-100 percent.

In one aspect, the present disclosure provides a method of manufacturing a single procedure device indicator, entailing (a) selecting a medical device, (b) preparing the indicator, where the indicator is a biocompatible composition comprising at least one filler and one or more binders that are present in the biocompatible composition at a predefined ratio by weight percentage, and (c) applying the biocompatible composition to the medical device to form at least one indicator region, where the at least one indicator region is configured to transition from an unmodified state to a modified state in response to an exposure. In illustrative embodiments the modified state of the at least one indicator region irreversibly identifies that the medical device has been subjected to the exposure after the single procedure.

In illustrative embodiments, the exposure entails contacting the medical device including the at least one indicator region with water, where the water contact occurs via one or more autoclave cycles, steam sterilization cycles, sterilization procedures, simple application of water and/or steam, aqueous disinfection, washing, and/or the sterile application of water or steam. In some embodiments, the exposure is one or more autoclave steam sterilization cycles. In some embodiments, the exposure comprises subjecting the device including the at least one indicator region to one or more steam sterilization cycles. In suitable embodiments, the one or more steam sterilization cycles are performed for a duration at temperatures and pressures sufficient to (i) transition the at least indicator region from the unmodified state to the modified state, and (ii) sterilize the device.

In some embodiments, the medical device is a single use orthopedic surgical device. In some embodiments, the medical device is selected from reamers, awls, rod benders, drill guides, guide tubes, distance gages, inserters, implant holders, clamps, portals, screwdrivers, spacers, distracters, plate benders, broaches, fusion plates, fusion screws, spinal rods, spinal connectors, artificial discs, tissue-anchoring devices, fixation devices, Stineman pins, dilators, joint spreaders, rasps, fusion cages, Kerrisons and Rongeurs, and combinations thereof. In certain embodiments, the biocompatible composition further entails one or more solvents, additives, accelerants, surfactants, emulsifiers, reducing agents, fluidizing agents, detergents, wetting agents, and dispersants, and combinations thereof.

In illustrative embodiments, the at least one filler is one or more superabsorbent polymers possessing a swelling capacity range of about 30-500 fold the volume of the one or more superabsorbent polymers prior to being subjected to the exposure. In some embodiments, the one or more superabsorbent polymers is selected from polyacrylates, polyacrylamides, polyacrylamide copolymers, polyacrylic acid, sodium polyacrylate, potassium polyacrylate, lithium polyacrylate, ammonium polyacrylate, ethylene maleic anhydride copolymer, carboxymethylcellulose, polyvinyl alcohol copolymers, polyethylene oxide, and copolymers of polyacrylonitrile, and combinations thereof. In some embodiments, the one or more binders are selected from alkyds, acrylics, vinyl-acrylics, polyurethanes, polyesters, melamine, epoxies, silanes, siloxanes, and oils, and combinations thereof.

In illustrative embodiments, the biocompatible composition further includes a solvent selected from xylene, toluene, alcohols, and ketones, and combinations thereof. In some embodiments, the one or more additives are selected from clays, kaolin, kaolinite, halloysite, diaspore, bentonite (Fuller's earth), ball clay, common clay, shale, fire clay, illite, chlorite, smectite minerals, quartz, limestone, silicate compounds, and quartz, and combinations thereof, in certain embodiments. In suitable embodiments, the predefined ratio of the at least one filler is at a range of about 30-90 by weight percentage in the biocompatible composition. In some embodiments, the predefined ratio of the one or more binders are at a range of about 10-70 by weight percentage in the present in the biocompatible composition. In certain embodiments, the one or more additives are present at a range of about 0.1-10 by weight percentage in the biocompatible composition.

In illustrative embodiments, the biocompatible composition of the indicator is prepared by mixing together the at least one filler and the one or more binders at the predefined ratios to produce a hydrogel slurry capable of transiting from the unmodified state to the modified state in response to the exposure. In some embodiments, the biocompatible composition further includes one or more solvents, additives, accelerants, surfactants, emulsifiers, reducing agents, fluidizing agents, detergents, wetting agents, and dispersants, and combinations thereof. In some embodiments, the predefined ratio of the at least one filler is present at a range of about 30-90 by weight percentage in the biocompatible composition, where the at least one filler is one or more superabsorbent polymers possessing a swelling capacity range of about 30-500 fold the volume of the one or more superabsorbent polymers prior to being subjected to the exposure. In illustrative embodiments, the methods further entail adding to the hydrogel slurry one or more solvents, additives, accelerants, surfactants, emulsifiers, reducing agents, fluidizing agents, detergents, wetting agents, and dispersants, and combinations thereof.

In some embodiments, the one or more solvents are selected from one or more of non-polar solvents, polar solvents, non-aqueous solvents, aqueous solvents, protic solvents, aprotic solvents, lipophilic solvents, hydrophilic solvents, water-miscible solvents, and water-immiscible solvents, and combinations thereof. In illustrative embodiments, the one or more binders are dissolved in the one or more solvents. In some embodiments, the one or more fillers, polymers and/or superabsorbent polymers (SAPs) are not miscible in the solvent. In suitable embodiments, the one or more solvents are selected from xylene, toluene, alcohols, and ketones, and combinations thereof.

In illustrative embodiments, the modified state of the at least one indicator region irreversibly identifies that the medical device has been subjected to the exposure after the single procedure, and wherein the exposure entails subjecting the medical device including the at least one indicator region to water contact, where the contact with water is selected from disinfection, washing, sterilizing, steam sterilization, and/or one or more autoclave cycles. In suitable embodiments, the medical device has a proximal end and a distal end, and where the at least one indicator region is positioned at or about the proximal end of the medical device. In suitable embodiments, the proximal end of the device and/or the indicator region is sufficiently located, configured, arranged and/or positioned on, or with respect to, the medical device such that the indicator region and/or proximal end of the device is not subjected to an exposure until after the single procedure.

In illustrative embodiments, the biocompatible composition is formulated such that after the biocompatible composition is applied to a proximal end of a device, i.e., constituting the indicator region, the superabsorbent polymer (SAP) is sterically arrange throughout the indicator region to ensure that water, when present, is able to contact—and accordingly swell—the SAP, i.e., the water is accessible to the SAP for adsorption via SAP surface exposure. Likewise, in some embodiments of the present invention, the SAP molecules are contiguously conformed or are arranged in a substantially contiguous configuration within the biocompatible composition, and consequently throughout the indicator region, such that water, when present, is able to continuously percolate the indicator region until the SAP swelling capacity is achieved.

In some embodiments, the biocompatible composition of the indicator is permanently adhered to the medical device as one or more coated layers or as an independently affixed layer by a surface application process selected from coating, painting, encapsulation, dip coated, immobilization, chemical adsorption, piezoelectric printing, thermal printing, coated rolling, roll-to-roll conveying, spray nozzle application, electroactive deposition, chemical vapor deposition, magnetoactive deposition, laser induction, and imprinting, and any combination thereof. In some embodiments, the biocompatible composition of the indicator is a material component of the device itself, e.g., the materials that constitute the device are composed of, inter alia, the biocompatible composition of the indicator.

In illustrative embodiments, the biocompatible composition is applied to the medical device by using a surface application process selected from coating, dip coating, encapsulating, chemical adsorption, immobilization, piezoelectric printing, thermal printing, coated rolling, roll-to-roll conveying, spray nozzle application, electroactive deposition, chemical vapor deposition, magnetoactive deposition, laser induction, and imprinting, and any combination thereof. In illustrative embodiments, the at least one indicator region is present as a surface layer on the medical device, and where the thickness of the surface layer is about 100 µm to 3 mm. The irreversible identification is a visual and tactile identification in certain embodiments. In some embodiments, the modified state of the at least one indicator region renders the device clinically impractical for reuse. In some embodiments, the one or more superabsorbent polymers is sodium polyacrylate. In some embodiments, the sodium polyacrylate possesses a degree of ionization ranging from about 30-100 percent.

In one aspect, the present disclosure relates to a single procedure device indicator, that include (a) a biocompatible composition comprising a superabsorbent polymer matrix, one or more binders, and one or more additives that are present in the biocompatible composition at predefined ratios by weight percentage in a mixture, solution and/or solvent, and (b) a surgical device at least partially enveloped or encapsulated by the biocompatible composition thereby forming at least one indicator region on the surgical device. The biocompatible composition is further composed of, in some embodiments, one or more accelerants, surfactants, emulsifiers, reducing agents, fluidizing agents, detergents, wetting agents, and dispersants, and combinations thereof.

In illustrative embodiments, the surgical device is a single use orthopedic surgical device. In some embodiments, the orthopedic surgical device is selected from reamers, awls, rod benders, drill guides, guide tubes, distance gages, inserters, implant holders, clamps, portals, screwdrivers, spacers, distracters, plate benders, broaches, fusion plates, fusion screws, spinal rods, spinal connectors, artificial discs, tissue-anchoring devices, fixation devices, Stineman pins, dilators, joint spreaders, rasps, fusion cages, Kerrisons and Rongeurs, and combinations thereof. In some embodiments, the surgical device possesses a proximal end and a distal end, where the at least one indicator region is located at or about the proximal end of the surgical device.

In illustrative embodiments, the superabsorbent polymer matrix is a hydrogel polymer possessing a swelling capacity range of about 30-500 fold the volume of the superabsorbent polymer matrix prior to being subjected to an exposure. In some embodiments, the hydrogel polymer is selected from polyacrylates, polyacrylamides, polyacrylamide copolymers, polyacrylic acid, sodium polyacrylate, potassium polyacrylate, lithium polyacrylate, ammonium polyacrylate, ethylene maleic anhydride copolymer, carboxymethylcellulose, polyvinyl alcohol copolymers, polyethylene oxide, and copolymers of polyacrylonitrile, and combinations thereof.

In suitable embodiments, the one or more binders are selected from alkyds, acrylics, vinyl-acrylics, polyurethanes, polyesters, melamine, epoxies, silanes, siloxanes, and oils, and combinations thereof. In some embodiments, the solvent is selected from xylene, toluene, alcohols, and ketones, and combinations thereof. In certain embodiments, the one or more additives are selected from clays, kaolin, kaolinite, halloysite, diaspore, bentonite (Fuller's earth), ball clay, common clay, shale, fire clay, illite, chlorite, smectite minerals, quartz, limestone, silicate compounds, and quartz, and combinations thereof, in certain embodiments. In illustrative embodiments, the predefined ratio of the superabsorbent polymer matrix is at a range of about 30-90 by weight percentage in the biocompatible composition. In illustrative embodiments, the predefined ratio of the one or more binders is at a range of about 10-70 by weight percentage in the biocompatible composition.

In suitable embodiments, the one or more additives are present at a range of about 0.1-10 by weight percentage in the biocompatible composition. In some embodiments, the biocompatible composition of the at least one indicator region is permanently affixed to the surgical device. In some embodiments, the at least one indicator region is composed of the biocompatible composition present as a surface layer on the surgical device, where the thickness of the surface layer is about 100 82 m to 3 mm. In some embodiments, the superabsorbent polymer matrix is a hydrogel formulation comprising sodium polyacrylate. In illustrative embodiments, the sodium polyacrylate possesses a degree of ionization ranging from about 30-100 percent.

In some embodiments, the biocompatible composition is present at predefined ratios by weight percentage in the mixture, solution and/or solvent, where the mixtures, solutions and/or solvents are characterized as non-polar, polar, non-aqueous, aqueous, protic, aprotic, lipophilic, hydrophilic, water-miscible, or water-immiscible, and/or combinations thereof. In illustrative embodiments, the one or more binders are dissolved in the one or more mixtures, solutions and/or solvents. In some embodiments, the one or more fillers, polymers and/or superabsorbent polymers (SAPs) are not miscible in the mixtures, solutions and/or solvents. In suitable embodiments, the one or more mixtures, solutions and/or solvents are selected from xylene, toluene, alcohols, and ketones, and combinations thereof.

In illustrative embodiments, the modified state of the at least one indicator region irreversibly identifies that the medical device has been subjected to the exposure after the single procedure, and wherein the exposure entails subjecting the medical device including the at least one indicator region to water contact, where the contact with water is selected from disinfection, washing, sterilizing, steam sterilization, and/or one or more autoclave cycles. In suitable embodiments, the medical device has a proximal end and a distal end, and where the at least one indicator region is positioned at or about the proximal end of the medical device. In suitable embodiments, the proximal end of the device and/or the indicator region is sufficiently located, configured, arranged and/or positioned on, or with respect to, the medical device such that the indicator region and/or proximal end of the device is not subjected to an exposure until after the single procedure.

In illustrative embodiments, the biocompatible composition is formulated such that after the biocompatible composition is applied to a proximal end of a device, i.e., constituting the indicator region, the superabsorbent polymer (SAP) is sterically arrange throughout the indicator region to ensure that water, when present, is able to contact—and accordingly swell—the SAP, i.e., the water is accessible to the SAP for adsorption via SAP surface exposure. Likewise, in some embodiments of the present invention, the SAP molecules are contiguously conformed or are arranged in a substantially contiguous configuration within the biocompatible composition, and consequently throughout the indicator region, such that water, when present, is able to continuously percolate the indicator region until the SAP swelling capacity is achieved.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE FIGURES

FIG. 1A shows hydrogen bonding between polymer matrix carboxylic acid groups and water molecules. FIG. 1B depicts hydrogen bonding between the carboxylate ion group groups of the polymer matrix and water molecules.

FIG. 3A shows the indicator before being subjected to steam sterilization, while FIG. 3B is a photograph of the indicators after steam sterilization.

FIG. 4A shows the coated indicator before water exposure, and FIG. 4B is a photograph of the coated indicators after exposure to water.

DETAILED DESCRIPTION

Figure 1A:
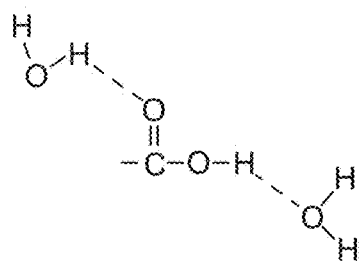
FIGS. 1A-1B are illustrative representations concerning the intermolecular interactions, such as hydrogen bonding, between polymer matrix functional groups and water molecules.

In the following detailed description, reference is made to the accompanying drawings, which form a part thereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

As used herein, unless otherwise stated, the singular forms "a," "an," and "the" include plural reference. Thus, for example, a reference to "an indicator" can include a plurality of indicators.

As used herein, the term "about" will be understood by persons of ordinary skill in the art and will vary to some extent depending upon the context in which it is used. If there are uses of the term which are not clear to persons of ordinary skill in the art, given the context in which it is used, the term "about" in reference to quantitative values will mean up to plus or minus 10% of the enumerated value.

As used herein, the terms "amphipathic" or "amphiphilic" are meant to refer to any material that is capable of polar and non-polar, or hydrophobic and hydrophilic, interactions. These amphipathic interactions can occur at the same time or in response to an external stimuli at different times. For example, when a specific material or coating, painting, encapsulation, and/or dip coating is said to be "amphipathic," it is meant that such material or coating, painting, encapsulation, and/or dip coating can be hydrophobic or hydrophilic depending upon external variables, such as, e.g., temperature, salinity, pH, etc.

The terms "assessing" and "evaluating" are used interchangeably to refer to any form of measurement, and includes determining if an element is present or not. The terms "determining," "measuring," "assessing," and "assaying" are used interchangeably and include both quantitative and qualitative determinations. Assessing may be relative or absolute. "Assessing the presence of" includes determining the amount of something present, as well as determining whether it is present or absent.

As used herein, the terms "binder" or "binders" refers to polymers or materials that facilitate adhesion, connection, coupling, binding, attachment, affixation, or joining of the biocompatible compositions of the indicators disclosed herein or the single-use indicators of the present disclosure to a substrate, e.g., a medical device. In some embodiments, the binders include, but are not limited to, alkyds, acrylics, vinyl-acrylics, polyurethanes, polyesters, melamine, epoxies, silanes, siloxanes, and oils, and combinations thereof. In some embodiments, the binder is dissolved in a solvent.

As used herein, the terms "biocompatible," "biocompatible material," "biocompatible polymer," "indicator," indicator materials," "materials," "polymer materials," or "biocompatible indicators" refer to a synthetic or natural material that is, for example, non-toxic to biological systems and/or congruent with biological processes. In this respect, biocompatibility of polymer materials denote minimal, negligible, or no risk of immunorejection, injury, damage and/or toxicity to living cells, tissues, organs, and/or biological systems. In illustrative embodiments, the biocompatible material is one or more superabsorbent polymers selected from, but not limited to, polyacrylates, polyacrylamides, polyacrylamide copolymers, polyacrylic acid, sodium polyacrylate, potassium polyacrylate, lithium polyacrylate, ammonium polyacrylate, ethylene maleic anhydride copolymer, carboxymethylcellulose, polyvinyl alcohol copolymers, polyethylene oxide, and copolymers of polyacrylonitrile, polylactic acid, polyglycolic acid, poly(lactide-co-glycolide), and/or poly(L-lactide), and the like, and combinations thereof.

As used herein, the term "composition" refers to a product with specified ingredients in the specified amounts, as well as any product which results, directly or indirectly, from combination of the specified ingredients in the specified amounts.

As used herein, the terms "device" or "instrument" refer to a substrate of which an indicator is applied to or affixed, where the indictor is representative of whether the device or instrument has been discharged. Typically, the devices and instruments of the present disclosure relate to single procedure medical devices and instruments, but are not necessarily limited thereto. In suitable embodiments, the medical device has a proximal end and a distal end, and where the at least one indicator region is positioned at or about the proximal end of the medical device. In suitable embodiments, the proximal end of the device and/or the indicator region is sufficiently located, configured, arranged and/or positioned on, or with respect to, the medical device such that the indicator region and/or proximal end of the device is not subjected to an exposure until after the single procedure.

In this respect, and in other words, the medical devices and instruments of the present disclosure include a proximal end and a distal end, where typically, for example, the distal end of the device or instrument is the functional region that, in illustrative embodiments, contacts the area of the patient being operated on, e.g., the distal end is typically not the device region contacted by the clinician or surgeon. The proximal end, on the other hand, for example, is the structural region that, in illustrative embodiments, is contacted by the clinician or surgeon. In other words, the proximal end or region of a medical device typically does not come into contact with a patient's bodily fluids, e.g., blood. In illustrative embodiments, the proximal end of the device is the region that, at least in part, is composed of or harbors the single-use indicators disclosed herein.

In some embodiments, the single procedure medical device is a single use orthopedic surgical device. In illustrative embodiments, the medical device or instrument is selected from, but not limited to, single-use reamers, awls, rod benders, drill guides, guide tubes, distance gages, inserters, implant holders, clamps, portals, screwdrivers, spacers, distracters, plate benders, broaches, fusion plates, fusion screws, spinal rods, spinal connectors, artificial discs, tissue-anchoring devices, fixation devices, Stineman pins, dilators, joint spreaders, rasps, fusion cages, Kerrisons and Rongeurs, and combinations thereof.

As used herein, the term "discharge status" of a single procedure device or instrument refers to the lifecycle status of the device or instrument. In suitable embodiments, for example, a device or instrument that has been "affirmatively discharged," as used herein, is an indication that the status of the device or instrument is an "end-of-use" status, i.e., the device should not be redeployed for a second or repeat procedure.

As used herein, the term "encapsulation" or "encapsulating" refers to the retention of substance within a compartment, delineated by a physical barrier. For example, the encapsulated agents described herein refer to agents which are retained within, and surrounded by a physical barrier, such as a capsule or nanocapsule. The term, "nanocapsule," as used herein, moreover, refers to a particle having a hollow core that is surrounded by a shell, such that the particle has a size of less than about 1,000 nanometers. When a nanocapsule includes an agent, the agent is typically located in the core that is surrounded by the shell of the nanocapsule.

As used herein, the term "exposure" refers to circumstances where a medical device, instrument, apparatus, biocompatible composition, indicator, indicator region, and/or an unmodified indicator region, alone or collectively, are subjected to one or more conditions, applications, and/or the presence of water, steam, sterilization, an autoclave cycle, aqueous disinfection or washing, the sterile application of water or steam, or other conditions where the medical device, instrument, apparatus, biocompatible compositions, indicator, indicator region, and/or the unmodified indicator region, alone or collectively, come into contact with water.

Along these lines, the biocompatible compositions of the present disclosure are formulated such that after a biocompatible composition is applied to a proximal end of a device, i.e., constituting the indicator region, the superabsorbent polymer (SAP) is sterically arrange throughout the indicator region to ensure that water, when present, is able to contact—and accordingly swell—the SAP, i.e., the water is accessible to the SAP for adsorption via SAP surface exposure. Likewise, in some embodiments of the present invention, the SAP molecules are contiguously conformed or are arranged in a substantially contiguous configuration within the biocompatible composition, and consequently throughout the indicator region, such that water, when present, is able to continuously percolate the indicator region until the SAP swelling capacity is achieved.

As used herein, the terms "hydrogel," "hydrogel matrix," "polymer matrix," or "matrix" are interchangeably used, and encompass polymer and non-polymer based matrices. Hydrogels, in this regard, as used herein, are typically continuous networks of hydrophilic polymers that absorb water. "Matrix" is also meant to refer to all other matrix or hydrogel compositions disclosed herein, including compositions that contain polymers, copolymers, terpolymer, and complexed polymer matrices, i.e., matrices that contain one, two, three, four or more monomeric or multimeric constituent units. The terms "hydrogel polymers" or "matrix polymer materials" refer to the materials used to make the matrices or hydrogels of the present disclosure. Such terms refer to both monomeric units of the materials and the polymers or co-polymers made therefrom.

As used herein, the term "polymer" refers to a macromolecule made of repeating monomer or multimer units. Polymers of the present disclosure are polymeric forms of, and include, but are not limited to, polyacrylates, polyacrylamides, polyacrylamide copolymers, polyacrylic acid, sodium polyacrylate, potassium polyacrylate, lithium polyacrylate, ammonium polyacrylate, ethylene maleic anhydride copolymer, carboxymethylcellulose, polyvinyl alcohol copolymers, polyethylene oxide, and copolymers of polyacrylonitrile, polylactic acid, polyglycolic acid, poly(lactide-co-glycolide), poly(L-lactide), poly(hyaluronic acid), poly(sodium alginate), poly(ethylene glycol), poly(lactic acid) polymers, poly(glycolic acid) polymers, poly(lactide-co-glycolides), poly(urethanes), poly(siloxanes) or silicones, poly(ethylene), poly(vinyl pyrrolidone), poly(2-hydroxy ethyl methacrylate), poly(N-vinyl pyrrolidone), poly (methyl methacrylate), poly(acrylic acid), poly(vinyl acetate), polyacrylamide, poly(ethylene-co-vinyl acetate), poly(methacrylic acid), polylactic acid, poly(L-lactide) (PLLA), polyglycolic acids, nylons, polyamides, polyanhydrides, poly(ethylene-co-vinyl alcohol, polycaprolactone, polyvinylhydroxide, poly(ethylene oxide), and polyorthoesters or a co-polymer or terpolymer formed from at least two or three members of the groups, respectively.

Along the same lines, the terms "superabsorbent polymer," "SAP," or "water-absorbing polymer," are interchangeably referred to herein, and encompass solutions or powders that possess the ability to absorb and retain large amounts of a liquid, e.g., water, relative to their own mass. In part, the properties of such water-absorbing polymers, which may be classified as hydrogels when cross-linked, can be attributed to the intermolecular interactions, e.g., hydrogen bonding, between the polymer material and water molecules. Depending on the ionic strength of any particular aqueous solution, SAP's as disclosed herein possess a swelling capacity, e.g., the ability to absorb one or more fluids, e.g., water, range of about 30-700 fold its weight in water compared to the weight or volume of the SAP as dry particulate matter, in a desiccated state, unsaturated state, or prior to being subjected to an exposure, as defined herein, water, and/or a sterilization cycle, and combinations thereof.

As used herein, "prevention" or "preventing" of an infection or condition refers to a method or indicator that, in a statistical sample, reduces the occurrence of the infection or condition in a sample patient population relative to an control sample patient population. As used herein, preventing an infection or condition includes the prevention of heath care associated infections, i.e., nosocomial infections, by preventing a second or subsequent use of a single procedure medical device or instrument.

As used herein, the term "solvent" refers to a liquid in which a solute is dissolved to form a solution. As disclosed herein, the polymers, superabsorbent polymers (SAPs), hydrogels and the like, typically are not miscible in a solvent, whereas the one or more binders as disclosed herein typically are miscible in a solvent as used herein. In some embodiments, one or more solvents are selected from one or more of non-polar solvents, polar solvents, non-aqueous solvents, aqueous solvents, protic solvents, aprotic solvents, lipophilic solvents, hydrophilic solvents, water-miscible solvents, and water-immiscible solvents, and combinations thereof. In illustrative embodiments, the one or more solvents are selected from xylene, toluene, alcohols, and ketones, and combinations thereof. As disclosed herein, although the term solvent typically refers to a liquid solution, the term "solution" does not necessarily invoke the term "solvent" as used herein. Likewise, the terms "slurry" and "mixture" are separate and distinct from a "solvent" as used herein.

As used herein, the terms "substantial" or "substantially" within the context of a "substantially enveloped" surface or region or a "substantially aligned" configuration, refer to, e.g., total or complete envelopment, encapsulation or alignment, and the like, but also includes lesser than complete or total envelopment, encapsulation or alignment, and the like, insofar as the intended purpose for performing the act can be carried out to the same extent as if the, e.g., envelopment, encapsulation or alignment, were total or complete. Likewise, in some embodiments of the present invention, the SAP molecules are contiguously conformed or are arranged in a "substantially contiguous configuration" within the biocompatible composition, and consequently throughout the indicator region, such that water, when present, is able to continuously percolate the indicator region until the SAP swelling capacity is achieved.

As used herein, the term "wettability" or "wetting" refers to the ability of a substance to maintain surface contact with a different substance or surface. Surface contact results from intermolecular interactions between a substance and the contacted surface. Wetting, and the surface forces that control wetting, are also responsible for other related effects, including capillary action or capillary effects. For example, when an indicator adheres to a surface of a device the wettability, or degree of wetting, can be calculated in terms of the force balance between the adhesive and cohesive forces. Wettability can be altered by, for example, adding different combinations and concentrations of materials to, for example, a biocompatible composition.

Single Procedure Indicators

When considering the potential for single procedure medical devices to become erroneously reintroduced into a surgical setting, i.e., after its initial—and presumptive only intended—use, the consequences can be severe. Whether intentional or otherwise, recirculation of single procedure devices precipitates a non-negligible health care expense both from a patient's well-being and an economic standpoint. See, e.g., Schultz, J. B., "Disposables in the O.R. 'Cover Story: Disposables, ECA Medical Instruments,'" (2013). Indeed, the impetus behind the advent of single-use medical instruments emanates directly from a desire to eliminate nosocomial infections. As single procedure devices became commonplace in the health care setting, various processes have been implemented to mitigate reprocessing and nosocomial pathogenesis.

Single procedure instruments, in this regard, provide a measure of mitigation with respect to persistent clinical concerns, e.g., acquired nosocomial infections, and economic costs, e.g., patient treatment and the associated increase in frequency and duration of hospital visits. The advantages of employing single-procedure instruments are not difficult to appreciate. Along these lines, some of the benefits attendant to using single procedure medical devices include, but are not limited to (i) decreased thermal necrosis of bone inasmuch as sharp, precise and accurate, surgical tools do not produce the same frictional consequences and osteological debris associated with the use of dull instruments, (ii) reduced surgical site contamination and accompanying infections, (iii) more efficient hospital inventory management insofar as the inventory burden is lessened with off-the-shelf kits for implants and related procedures, (iv) improved patient safety and clinician confidence, and (v) the elimination of substantial life-cycle support costs and associated carbon footprint encumbrances, e.g., cleaning, handling and re-sterilization of reusable medical devices.

There remains a need, however, for readily ascertainable indications that conspicuously identify when single procedure instruments are at their end-of-use. Such indicators would markedly decrease the possibility of health care related infections associated with the unintentional reuse of single procedure devices. Nosocomial infections and surgical errors are coterminous with respect to the use of recycled single procedure devices, i.e., at least to the extent that post process disinfection and sterilization is typically not extensive, while the cause of field failure concerning single-use devices similarly stems from second or repeated procedures with devices that may only be calibrated for a single procedure. As such, the import of addressing the foregoing issues by having a very distinct indication that a single procedure device has been discharged is readily apparent, where ensuring that such devices are not placed back in the operating room is a lingering health care dilemma.

Following a surgical operation, as noted above, end-of-use single procedure devices typically undergo one or more disinfection and/or sterilization cycles before they are ultimately discarded. In many instances, such sterilization cycles are performed via an autoclave, where, in the presence of elevated temperatures and pressures, water becomes superheated steam that consequently functions to sterilize the enclosed contents of the autoclave. Likewise, disinfection of single procedure devices, or simple washing, may also occur prior to, after, or to the exclusion of a steam sterilization cycle. Similar to steam sterilization, in this respect, such disinfection or washing also subjects the single procedure device to the presence of water. An aspect of the present invention takes advantage of these processes by developing water-sensitive, steam-sensitive, water-absorbing, materials that serve as single-use indicators when applied or connected to any device or instrument that will be or has been subjected to the water and/or steam sterilization.

In illustrative embodiments, the single use indicators of the present invention operate in a distinct and irreversible manner as further detailed herein. Some embodiments of the present invention relate to indicator materials that are one or more superabsorbent polymers possessing a swelling capacity range of about 30-700 fold the volume of the superabsorbent prior to being subjected to a steam sterilization cycle. One non-limiting example of a superabsorbent polymer of the present invention is sodium polyacrylate. Ionized forms of sodium polyacrylate, and related materials with similar properties as further detailed herein, experience a substantial increase in volume and morphological changes when subjected to water, e.g., steam sterilization. Such distinct indications impart both a visual and tactile modification thereby providing health-care personnel with readily ascertainable indications that the device has been steam sterilized, and accordingly is at its end-of-use.

To the extent that other indicator techniques have been previously disclosed, see e.g., U.S. Pat. No. 8,567,338, disclosing reprocessing indicators for single patient use medical instruments, and U.S. Pat. No. 8,157,747, describing single-use indicators for surgical instruments, those and related systems concern reversible colorimetric indicators that fail to provide an irreversible visual and tactile change or modification associated with sterilization processes. Equally as important with respect to the present single-use indicators is the mechanism underlying the indicator modification, which elicits a volumetric and morphological modification that is not dependent upon a user's ability to ascertain reversible color changes that may be less than apparent.

Along these lines, superabsorbent materials, such as, for example, water-absorbing polymers, are macromolecules composed of one or more hydrophilic backbones. These polymers typically contain carboxylic acid functional groups, and salts or esters thereof, which, depending on their ionization state in solution, may be present as the conjugate base of carboxylic acid moieties, i.e., carboxylate ions. These functional groups impart the hydrophilic nature of such polymers via hydrogen bonding interactions that occur between the electronegative oxygen atoms and electron deficient hydrogen atoms when in an aqueous solution. See FIG. 1. The polymer matrices of the present invention are considered superabsorbent polymers, in illustrative embodiments, due to the fact that either conjugate form, i.e., the carboxylic acid and carboxylate ion groups, of the polymers electrostatically bond with water molecules. See FIG. 1A and FIG. 1B. In concert with decreasing the energy of a system, these intramolecular interactions function to disperse the polymers of the present invention in an aqueous solution, which results in an increase in system entropy.

The polymer chains of the present indicators, in illustrative embodiment, form a three dimensional lattice via cross-linking. This network structure matrix therefore not only increases in volume by permitting matrix hydration, but also remains in the hydrated state inasmuch as the cross-linked polymers prevent the dissemination of water molecules. Put simply, when the water-absorbing polymers, as disclosed herein, are present as, for example, a sodium salt of the carboxylic acid conjugate base, this sodium carboxylate in solution produces as osmotic imbalance. These hydrated sodium ions, albeit fluid in solution, cannot disperse from the gel lattice, which consequently imparts an irreversible indicator as described herein. The enhanced hydrophilicity of the polymer matrix indicators of the present invention, i.e., their ability to absorb and retain water, is referred to as the material's swelling capacity.

In some embodiments, the swelling capacity range of the one or more polymers, superabsorbent polymers, polymer matrices, hydrogels and/or indicator materials of the present invention is from about 10, 50, 100, 200, 300, 400 or 500-fold to from about 300, 400, 500, 600, 700, 800, 900 or 1000-fold the weight or volume of the one or more superabsorbent polymers, polymer matrices, polymers, hydrogels and/or indicator materials of the present invention prior to being hydrated per an exposure. In illustrative embodiments, the swelling capacity range of the one or more polymers, superabsorbent polymers, polymer matrices, hydrogels and/or indicator materials of the present invention is from about 300, 400 or 500-fold to from about 600, 700 or 800-fold the weight or volume of the one or more superabsorbent polymers, polymer matrices, polymers, hydrogels and/or indicator materials of the present invention prior to being hydrated per an exposure.

In this regard, the biocompatible compositions of the present disclosure are formulated such that after the biocompatible composition is applied to a proximal end of a device, i.e., constituting the indicator region, the superabsorbent polymer (SAP) is sterically arrange throughout the indicator region to ensure that water, when present, is able to contact—and accordingly swell—the SAP, i.e., the water is accessible to the SAP for adsorption via SAP surface exposure. Likewise, in some embodiments of the present invention, the SAP molecules are contiguously conformed or are arranged in a substantially contiguous configuration within the biocompatible composition, and consequently throughout the indicator region, such that water, when present, is able to continuously percolate the indicator region until the SAP swelling capacity is achieved.

In some embodiments, the hydration of the one or more polymers, superabsorbent polymers, polymer matrices, hydrogels and/or indicator materials of the present invention is through an exposure. In suitable embodiments, the exposure is an exposure to water, e.g., via steam sterilization, or super-heated steam. In some embodiments, the water, steam and/or super-heated steam exposure occurs in an autoclave. In certain embodiments, one or more autoclave cycles are used as the exposure. Steam autoclave exposures can be performed using one or more of a gravity cycle, pre-vacuum cycle, steam flush pressure pulse cycle, and post-vacuum cycles. It will be readily apparent to one skilled in the art that the foregoing and various other steam sterilization cycles, as well as other aqueous sterilization procedures, can be implemented with respect to the present invention insofar as such cycles entail the requisite moisture, temperature, and/or pressures required to transition the indicators, in some embodiments, from an unmodified state to a modified state.

In some embodiments of the present invention, the exposure is one or more autoclave gravity cycles, pre-vacuum cycles, steam flush pressure pulse cycles, and post-vacuum cycles. In illustrative embodiments, the exposure is one or more autoclave gravity cycles. A non-limiting example of an autoclave gravity cycle steam sterilization procedure entails temperatures ranging from about 200, 300 or 400° F. or ° C. to from about 300, 400 or 500° F. or ° C. In some embodiments, the autoclave cycle is performed at about 274° F. The duration of an autoclave cycle, in suitable embodiments, ranges from about 5, 10, 15, 20, 25 or 30 minutes (min) or hours (h) to about from 15, 20, 25, 30, 40 or 50 minutes (min) or hours (h). In some embodiments, the duration of an autoclave cycle is about 18-20 minutes followed by an equal amount of time in a drying cycle.

It will be readily apparent to the skilled artisan that numerous additional variables can impact the rate and extent of indicator modification, polymerization, swelling, solidification, and/or congealing, etc. Such factors include, for example, percent humidity or hydration, $CO_2$ concentration, and/or temperature, etc., associated with an autoclave cycle. The skilled artisan will readily appreciate that appropriate adjustments can optimize indicator volume, size, weight, morphology, consistency, viscosity and overall indication appearance and texture for specific or desired uses.

In one aspect, the present disclosure relates to a single-use device indicator that includes a biocompatible composition composed of one or more of a filler, polymer, matrix, hydrogel, indicator materials, and/or a superabsorbent polymer matrix. The composition is "biocompatible," to the extent that the foregoing materials are low- or non-toxic to biological systems and/or congruent with biological processes. In this respect, biocompatibility of the materials present minimal or no risk of immunoreactivity, injury, damage and/or toxicity to living cells, tissues, organs, and/or biological systems.

In illustrative embodiments, the one or more fillers, polymers, matrices, hydrogels, indicator materials, and/or superabsorbent polymer matrices are, for example, but not limited to, monomers, copolymers, terpolymers and/or polymers, and salts, esters, and ionized conjugates, of one or more of polyacrylates, polyacrylamides, polyacrylamide copolymers, polyacrylic acid, sodium polyacrylate, potassium polyacrylate, lithium polyacrylate, ammonium polyacrylate, ethylene maleic anhydride copolymer, carboxymethylcellulose, polyvinyl alcohol copolymers, polyethylene oxide, polyacrylonitrile, polylactic acid, polyglycolic acid, poly(lactide-co-glycolide), poly(L-lactide), silicone acrylate, acrylate with enhanced hydrophilic surface functionality, siloxane acrylate, hexafocon A, enflufocon A, enflufocon B, hioxifilcon B, hioxifilcon D, hioxifilcon A, polymacon, methafilcon A, 2-hydroxyethyl methacrylate (2-HEMA), 2,3-dihydrosypropryl methacrylate (Glycerol Methacrylate, GMA), polymethyl methacrylate (PMMA), acrylamide, poly(hyaluronic acid), poly(sodium alginate), poly(ethylene glycol) (PEG), poly(lactic acid) polymers, poly(glycolic acid) polymers, poly(lactide-co-glycolides) (PLGA), poly (urethanes), poly(siloxanes) silicones, poly(ethylene), poly (vinyl pyrrolidone), poly(2-hydroxy ethyl methacrylate), poly(N-vinyl pyrrolidone), poly(methyl methacrylate), poly (vinyl alcohol) (PVA), poly(acrylic acid), poly(vinyl acetate), polyacrylamide, poly(ethylene-co-vinyl acetate), poly(methacrylic acid), polylactic acid (PLA), poly(L-lactide) (PLLA), polyglycolic acids (PGA), polyamides, polyanhydrides, poly(ethylene-co-vinyl alcohol) (EVOH), polycaprolactone, polyvinylhydroxide, poly(ethylene oxide) (PEO), polyorthoesters, poly(N-isopropylacrylamide) (PIPAAm), N,N-dimethylaminopropyl acrylamide (DMAPAAm), poly(N-acryloylpiperidine)-cysteamine (pAP), PIPAAM-carboxymethyl dextran benzylamide sulfonate/sulfate (PIPAAm-CMDBS), N,N-methylene-bis-acrylamide cross-linked polymer, PIPAAm-PEG N-isopropylacrylamide, N,N-dimethylacrylamide, 2-hydroxyethylmethacrylate, N-hydroxyethyl acrylamide, N-vinyl-2-pyrrolidone, 4-pentenoic acid, N-isopropyl methacrylamide, N-methoxymethyl-N- isopropylacrylamide, 2-(dimethylmaleimido)-N-ethylacrylamide, N,N-methylene-bis-acrylamide and PIPAAm-PEG, and combinations thereof including cross-linked polymers, co-polymers and/or terpolymers thereof, and combinations thereof.

Examples of acceptable salts include, but are not limited to, cationic salts, such as, but not limited to, sodium, potassium, lithium, calcium, magnesium, ammonium and alkylammonium; sulfates, phosphates, mesylates, bismesylates, tosylates, lactates, tartrates, malates, bis-acetates, citrates, bishydrochloride salts, acid addition salts of inorganic acids such as hydrochloric, orthophosphoric, sulfuric, phosphoric, nitric, carbonic, boric, sulfamic and hydrobromic acids; or salts of organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric and orotic acids. Salts of amine groups may also comprise quaternary ammonium salts in which the amino nitrogen atom carries a suitable organic group such as an alkyl, alkenyl, alkynyl or aralkyl moiety. The salts may be formed by conventional means, such as by reacting the free base form of the compound with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

In illustrative embodiments, the one or more fillers, polymers, matrices, hydrogels, indicator materials, and/or superabsorbent polymer matrices are polyacrylic acid and/or sodium polyacrylate. While such biocompatible compositions are employed with respect to the present technology, in suitable embodiments, substantially similar compositions may be used in certain embodiments. Such substantially similar compositions include, but are not limited to, e.g., related molecules, materials, compounds, polymers, and compositions possessing a similar or identical functional and/or structural profile or are coterminous with the physical propertied of the compositions used herein. With respect to the biocompatible composition properties, characteristics or parameters, which allow for a substantially similar or identical indicator matrices to precipitate, these compositions are also acceptable in suitable embodiments. Likewise, the present disclosure contemplates one or more structures, conjugates, compounds, compositions and the like, consistent with the absorbance profile, swelling capacity, molecular and/or steric profiles, conformation, structural and/or empirical formulations, stoichiometric ratios, spectrophotometric profiles, NMR profiles, refractive indices, liquid transition temperatures, and/or other data profiles consistent with the present compositions.

The biocompatible composition of the single-use device indicators of the present disclosure also include one or more binders and/or one or more additives that are present in the biocompatible composition at predefined ratios by weight percentage in a solvent or solution at predefined ratios by weight percentage with respect to the biocompatible composition. The binders, for example, include, but are not limited to, alkyds, acrylics, vinyl-acrylics, polyurethanes, polyesters, melamine, epoxies, silanes, siloxanes, and oils, and combinations thereof. Non-limited examples of suitable epoxies in this respect include non-aromatic based epoxy resins, aliphatic epoxy resins, alicyclic epoxy resins, TGIC, epoxy resins with rings containing nitrogen such as a hydantoin epoxy resin, a hydrogenated epoxy resin, aliphatic epoxy resins, glycidyl ether type epoxy resins, dicyclo-type epoxy resins, and a naphthalene type epoxy resins, and combinations thereof.

The binders in this regard function to secure the polymer indicators of the present invention to the single procedure device or to encapsulate the device, where, in some embodiments, the binder and/or biocompatible composition of the indicator is a material component of the device itself, i.e., it is coterminous with the structure of the device. The binders of the present invention facilitate the attachment of the biocompatible indicator composition to the single procedure device in illustrative embodiments. In some embodiments, the at least one indicator region is permanently affixed to the device. In other embodiments, the biocompatible composition of the indicator is a material component of the device itself, e.g., the materials that constitute the device are composed of, inter alia, the biocompatible composition of the indicator.

In illustrative embodiments, the biocompatible composition of the indicator is permanently adhered to the medical device as one or more coated layers or as an independently affixed layer by a surface application process selected from coating, painting, encapsulation, dip coating, spray drying, chemical adsorption, piezoelectric printing, thermal printing, coated rolling, roll-to-roll conveying, spray nozzle application, electroactive deposition, chemical vapor deposition, magnetoactive deposition, laser induction, imprinting, deposition, and immobilizing, and any combination thereof. As used herein, the term "immobilizing" refers to the ability to retain the biocompatible composition of the indicator in or on a device surface, component, region or matrix. In some embodiments, immobilization also refers to, but is not limited to, adsorption, covalent binding, entrapment, membrane confinement, and cross-linking.

Additionally or alternatively, the indicator compositions of interest can be conjugated to a solid support, such as a bead or other material, which is subsequently affixed to the devices and instruments of the present invention or is a component material of such apparatuses. In addition, a first solid support such as a bead can also be conjugated, if desired, to a second solid support, which can be a second bead, the device or instrument, and/or other support structures, by any suitable means, including those disclosed herein for conjugation of a polymer or other material to support, device and/or instruments as disclosed herein. In some embodiments, the at least one indicator region is permanently affixed to the device. While in other embodiments, the biocompatible composition of the indicator is a material component of the device itself, e.g., the materials that constitute the device are composed of, inter alia, the biocompatible composition of the indicator.

The devices of the present invention, moreover, have a proximal end and a distal end, where the at least one indicator region is positioned at or about the proximal end of the medical device. In suitable embodiments, the proximal end of the device and/or the indicator region is sufficiently located, configured, arranged and/or positioned on, or with respect to, the medical device such that the indicator region and/or proximal end of the device is not subjected to an exposure until after the single procedure.

Certain embodiments of the present invention include deposition techniques, such as, e.g., piezoelectric ink-jet processes (see, e.g., U.S. Pat. Nos. 7,051,654 and 5,668,581 and U.S. Pat. Pub. No. 2010/0033545), including single or multiplex configurations (see, e.g., U.S. Pat. No. 6,997,550), liquid nozzle spray (see, e.g., U.S. Pat. Pub. No. 2009/0087896), electroactive deposition processes (see, e.g., U.S. Pat. Pub. No. 2002/0008746), magnetoactive deposition processes, laser-induced forward transfer processes, laser printing utilizing nano-laser and femto-laser technologies and/or polydimethylsiloxane (PDMS) stamp for microcontact printing. All of the foregoing patents and patent publications are hereby incorporated by reference in their entirety.

Solvents and solutions used in some embodiments of the present invention are typically inert insofar as the solvent or solution do not manifest physical, biological and/or chemical properties that would be deleterious to the intended use and/or purpose of the present invention. In suitable embodiments, the biocompatible composition is present at predefined ratios by weight percentage in a mixture, solution and/or solvent, where the mixtures, solutions and/or solvents are characterized as non-polar, polar, non-aqueous, aqueous, protic, aprotic, lipophilic, hydrophilic, water-miscible, or water-immiscible, and/or combinations thereof. In illustrative embodiments, the one or more binders are dissolved in the one or more mixtures, solutions and/or solvents. In some embodiments, the one or more fillers, polymers and/or superabsorbent polymers (SAPs) are not miscible in the mixtures, solutions and/or solvents. In suitable embodiments, the one or more mixtures, solutions and/or solvents are selected from xylene, toluene, alcohols, and ketones, and combinations thereof.

In particular, with respect to the solvents of the present invention, in some embodiments, the solvent is selected from xylene, toluene, alcohols, and ketones, and combinations thereof. In certain embodiments, a solvent is not used to form the biocompatible compositions of the indicator. In some embodiments, one or more solvents are used to form the biocompatible compositions of the indicator. In this respect, illustrative embodiments of the present invention include one or more binders dissolved in a solvent.

The above-mentioned biocompatible compositions, fillers, binders, solvents, polymers, matrices, hydrogels, indicator materials, and/or superabsorbent polymer matrices may further contain an appropriate additive depending on purposes and efficacy of the additive to the overall functionality of the indicator. Examples of the above-mentioned additives include, but are not limited to, one or more second or additional fillers, binders, and solvents, while such additives may also include, for example, accelerants, surfactants, emulsifiers, reducing agents, fluidizing agents, detergents, wetting agents, dispersants, diluents, antioxidants, denaturants, dyes, pigments, discoloration inhibitors, UV absorbers, softening agents, stabilizers, plasticizers, antifoaming agents, reinforcing agents, hardening agents, hardening-accelerator agents, binding conjugates, curing agents and/or other constituents, and combinations thereof. In certain embodiments, the one or more additives are not used to form the biocompatible compositions of the indicator. In other embodiments, one or more additives are used to form the biocompatible compositions of the indicator.

Viscosity agents include, but are not limited to, methylcellulose, polyvinyl alcohol, starch, and combinations or mixtures thereof. The kind, number, and amount of additives contained in a composition, and more specifically in a biocompatible composition, may be appropriately set depending on purposes. Exemplary additives of the present disclosure include, but are not limited to, one or more clays, kaolin, kaolinite, halloysite, diaspore, bentonite (Fuller's earth), ball clay, common clay, shale, fire clay, illite, chlorite, smectite minerals, quartz, limestone, silicate compounds, and quartz, and combinations thereof, in certain embodiments. In certain embodiments, the one or more additives are not used to form the biocompatible compositions of the indicator. In other embodiments, one or more additives are used to form the biocompatible compositions of the indicator.

In illustrative embodiments, one or more of the at least one filler, one or more binders, one or more additives, and the solvent, alone, collectively, and in various combinations, are combined to form a mixture at predefined ratios. These particular predefined ratios or concentrations that provide for the biocompatible composition of the indicator material to function in accord with its intended use as an irreversible indicator of water exposure and/or steam sterilization—which is coterminous with an end-of-use discharge status for such devices—while also possessing characteristics that allow for such compositions to at least partially envelope, encapsulate, contact, integrate, intercalate, bind, affix, adhere and/or couple, and the like, to a surgical device thereby forming at least one indicator region as detailed herein.

In certain embodiments, the one or more fillers, polymers, matrices, hydrogels, indicator materials, and/or superabsorbent polymer matrices are present at a predefined ratio in the biocompatible composition at a range of about 0.001, 0.01, 0.1, 1, 5, 10, 20, 30 or 40% by dry weight percentage or (w/v) to from about 40, 50, 60, 70, 80, 90, 95 or 99% by dry weight percentage or (w/v). In some embodiments, the one or more fillers, polymers, matrices, hydrogels, indicator materials, and/or superabsorbent polymer matrices are present at a predefined ratio in the biocompatible composition at a range of about 30% by dry weight percentage or (w/v) to from about 90% by dry weight percentage or (w/v).

Illustrative embodiments of the present invention, for example, entail a predefined ratio of the one or more binders in the biocompatible composition at a range of about 0.001, 0.01, 0.1, 1, 5, 10, 20, 30 or 40% by dry weight percentage or (w/v) to from about 40, 50, 60, 70, 80, 90, 95 or 99% by dry weight percentage or (w/v). In some embodiments, the one or more binders are present at a predefined ratio in the biocompatible composition at a range of about 10% by dry weight percentage or (w/v) to from about 70% by dry weight percentage or (w/v). Regarding exemplary embodiments of biocompatible composition disclosed herein, some include one or more additives present at predefined ratio range of about 0.001, 0.01, 0.1, 1, 5, 10, 20, 30 or 40% by dry weight percentage or (w/v) to from about 40, 50, 60, 70, 80, 90, 95 or 99% by dry weight percentage or (w/v). In suitable embodiments, the one or more additives are present in an amount from about 0.1% by dry weight percentage or (w/v) to about 10% by dry weight percentage or (w/v). In other embodiments, an additive is not a component of the biocompatible composition of the indicator.

In some embodiments, at least one solvent is employed at a predefined ratio or concentration in the biocompatible composition at a range of about 0.001, 0.01, 0.1, 1, 5, 10, 20, 30 or 40% by dry weight percentage or (w/v) to from about 40, 50, 60, 70, 80, 90, 95 or 99% by dry weight percentage or (w/v). In suitable embodiments, the at least one solvent is present in an amount from about 0.1% by dry weight percentage or (w/v) to about 60% by dry weight percentage or (w/v). In other embodiments, a solvent is not a component of the biocompatible composition of the indicator. Concentrations or predefined ratios of the one or more fillers, binders, additives and solvents are also determined, in certain embodiments, such that the intended properties of the resulting biocompatible composition and indicator regions are in accord with the intended use of the present disclosure. The skilled artisan will readily recognize that various concentrations and combinations of the foregoing materials can be applied for a desired use.

Insofar as the biocompatible compositions forming the indicator region, material, layer, composition, component, and the like, is a material component of the device itself, i.e., it is coterminous with the structure of the device, and/or are permanently attached, adhered or coupled to the devices of the present disclosure, e.g., as an independently affixed layer by a surface application process, such devices in suitable embodiments are selected from, but not limited to, single use surgical devices, orthopedic surgical devices, reamers, awls, rod benders, drill guides, guide tubes, distance gages, inserters, implant holders, clamps, portals, screwdrivers, spacers, distracters, plate benders, broaches, fusion plates, fusion screws, spinal rods, spinal connectors, artificial discs, tissue-anchoring devices, fixation devices, Stineman pins, dilators, joint spreaders, rasps, fusion cages, Kerrisons and Rongeurs, and combinations thereof.

In this regard, the devices of the present invention typically have a proximal end and a distal end, where, for example, the distal end of the device or instrument is the functional region that, in illustrative embodiments, contacts the area of the patient being operated on, e.g., the distal end is typically not the device region contacted by the clinician or surgeon. The proximal end, on the other hand, for example, is the structural region that, in illustrative embodiments, is contacted by the clinician or surgeon, which typically does not come into contact with a patient's bodily fluids, e.g., blood. In illustrative embodiments, the proximal end of the device is the region that, at least in part, is composed of or harbors the single-use indicators disclosed herein. Some embodiments of the present invention, however, provide for various, additional and/or alternative locations on the medical device that encompasses an indicator region.

In illustrative embodiments, the modified state of the at least one indicator region irreversibly identifies that the medical device has been subjected to the exposure after the single procedure, and wherein the exposure entails subjecting the medical device including the at least one indicator region to water contact, where the contact with water is selected from disinfection, washing, sterilizing, steam sterilization, and/or one or more autoclave cycles. In suitable embodiments, the medical device has a proximal end and a distal end, and where the at least one indicator region is positioned at or about the proximal end of the medical device. In suitable embodiments, the proximal end of the device and/or the indicator region is sufficiently located, configured, arranged and/or positioned on, or with respect to, the medical device such that the indicator region and/or proximal end of the device is not subjected to an exposure until after the single procedure.

To the extent that the biocompatible compositions forming the indicator region, material, layer, composition, component, and the like, are permanently attached, adhered or coupled to the devices of the present disclosure, e.g., as an independently affixed layer by a surface application process, such a layer, in some embodiments can be one or more layers. Nevertheless, the one or more layers of the biocompatible compositions forming the indicator region are applied to the device, as detailed herein, at a depth or thickness. The depth or thickness of the indicator surface layer, in illustrative embodiments, is from about 0.001, 0.01, 0.1, 1, 0.25, 0.5, 0.75, 1, 3, 5, 7, 9, 10, 15, 20, 30, 50, 100, 500, or 900 nm, µm or mm to about 0.1, 0.25, 0.5, 0.75, 1, 3, 5, 7, 9, 10, 15, 20, 30, 50, 100, 500, or 900 nm, µm or mm. In other embodiments, the depth or thickness is from about 0.001, 0.01, 0.1, 1, 0.25, 0.5, 0.75, 1, 3, 5, 7, 9, or 10 nm, µm or mm to from about 0.5, 0.75, 1, 3, 5, 7, 9, 10, 15, 20, 30, 50, or 100 nm, µm or mm. In suitable embodiments, the depth or thickness of the layer is about 10 µm to 3 mm.

In illustrative embodiments, the biocompatible composition is formulated such that after the biocompatible composition is applied to a proximal end of a device, i.e., constituting the indicator region, the superabsorbent polymer (SAP) is sterically arrange throughout the indicator region to ensure that water, when present, is able to contact—and accordingly swell—the SAP, i.e., the water is accessible to the SAP for adsorption via SAP surface exposure. Likewise, in some embodiments of the present invention, the SAP molecules are contiguously conformed or are arranged in a substantially contiguous configuration within the biocompatible composition, and consequently throughout the indicator region, such that water, when present, is able to continuously percolate the indicator region until the SAP swelling capacity is achieved.

Single Procedure Indicator Methods and Applications

In one aspect, the present disclosure provides a method of manufacturing a single procedure device indicator, entailing (a) selecting a medical device; (b) preparing the indicator, where the indicator is a biocompatible composition with at least one filler and one or more binders that are present in the biocompatible composition at a predefined ratio by weight percentage, and (c) applying the biocompatible composition to the medical device to form at least one indicator region, where the at least one indicator region is configured to transition from an unmodified state to a modified state in response to an exposure. In illustrative embodiments the modified state of the at least one indicator region irreversibly identifies that the medical device has been subjected to the exposure after the single procedure.

The biocompatible composition is prepared in some embodiments by mixing together the at least one filler and the one or more binders at the predefined ratios detailed herein. In certain embodiments, the biocompatible composition further includes one or more solvents, additives, accelerants, surfactants, emulsifiers, reducing agents, fluidizing agents, detergents, wetting agents, and dispersants, and combinations thereof. These components, in various combinations and concentrations, i.e., appropriate for forming the compositions and indicators of the present invention, are combined or mixed at a temperature, pH, gas concentration, e.g., $O_2$, $CO_2$, nitrogen levels, etc., salinity, ionic concentration, etc., and for a duration of time sufficient to produce an indicator slurry, solution, emulsion, sols, gel, semi-solid, gel-sol, aggregate composition, paste, material, paint, coating, dip coating, and the like, capable of transiting from the unmodified state to the modified state in response to the exposure.

For example, some embodiments of the present invention include, but are not limited to, providing a filler solution of about 30-90 by weight percentage in the biocompatible composition, where the filler composition or solution is combined with a binder composition or solution, for example, in some embodiments, one or more binders in a solvent, of about 10-70 by weight percentage of the binder composition or solution in the biocompatible composition at room temperature (RT) for about 5 minutes to about 3 hours with stirring. Additionally or alternatively the foregoing solutions and/or compositions may also contain one or more additives that are present at a range of about 0.1-10 by weight percentage in the biocompatible composition, while some embodiments further entail one or more suitable solvents at a range of about 0.1-60 by weight percentage in the biocompatible composition.

The present mixtures are combined, reacted, mixed, etc., for a sufficient time, at an appropriate temperature to produce a formulation with the desired physical and chemical properties, e.g., viscosity, purity, adherence, boiling point, density, osmotic polarity, colloidal consistency, hydrophilicity, hydrophobicity, etc., to ensure that, depending on the intended application as described herein, the biocompatible composition of the indicator region is capable of functioning as a component or constituent of a device, i.e., it is configured to transition from an unmodified state to a modified state in response to an exposure.

The slurries, solutions, emulsions, sols, gels, semi-solids, gel-sols, aggregate compositions, pastes, materials, paints, coatings, dip coatings, and the like, of the present invention are also subjected to other processes and techniques to achieve the desired composite characteristics of the present biocompatible composition of the indicator region or material. Some of these processes and techniques, include, but are not limited to, subjecting the foregoing mixtures to one or more of centrifugation, drying, desiccating, buffering, chromatography, exchange resin chromatography, size exclusion chromatography, concentration, dilution, distillation, heating, cooling, suspending, reacting, precipitating, homogenizing, saturating, unsaturation techniques, and solubilizing, and the like, and combinations thereof.

Methods for producing the biocompatible composition of the indicator also include, in certain embodiments, mixing one or more of the fillers, binders, additives and/or solvents to form a congealed matrix or otherwise suitable biocompatible composition state. In this regard, illustrative embodiments of the present disclosure provide for a filler, binder, additive, and/or solvent mixture at a final concentration from about 0.001, 0.01, 0.1, 0.5, 1, 1.5, 2, 2.5, 3, 3.5, 4, 5, 10, 20, 30, 40, 50, 60, 70, 80 or 90% (w/v) of the filler, binder, additive, and/or solvent mixture to from about 1, 5, 10, 20, 30, 40, 50, 60, 70 80, 90 or 9% (w/v) of the filler, binder, additive, and/or solvent mixture.

Mixing the one or more fillers, binders, additives, and/or solvents into a slurry or solution at a final concentration can be performed by various methods known in the art. It will be readily apparent to the skilled artisan that heating a mixture, slurry, and/or solution to about 30, 40, 50, 60, 70, 80, 90, 100, 110, 120, or 130° F. or ° C., or higher temperatures, for about 5-60 minutes min or hours will, thereby, sufficiently mix, disperse, and/or dissolve the one or more fillers, binders, additives, and/or solvents. In illustrative embodiments, after mixing the foregoing components the final mixture, slurry and/or solution is subsequently cooled to room temperature.

The pH of the mixture, slurry and/or solutions of the present disclosure is, in suitable embodiments, sufficient to facilitate the generation of a biocompatible composition of the indicator region interactions. In illustrative embodiments, the pH ranges from about 1, 2, 3, 4, 5, 6, 7 or 8 to from about 5, 6, 7, 8, 9, 10, 11, 12, 13 or 14. In some embodiments, the pH ranges from about 5, 6, 7 or 8 to from about 6, 7, 8 or 9. In illustrative embodiments, the pH is about 7 or 7.4, i.e., physiological pH.

The polymers, materials, compositions and/or hydrogels of the present disclosure are allowed to properly congeal, in some embodiments, in order to facilitate a suitable composition to function as the indicator. In illustrative embodiments, the polymers and/or hydrogels are allowed to congeal for about 0.001, 0.01, 0.1, 0.5, 1, 2, 3, 4, 5, 6, 7, 8, 9, 10, 20, 30, or 50 hours (h). It will be readily apparent to the skilled artisan that numerous additional variables can effect polymerization, solidification, or congealing. Such factors include, for example, hydration, humidity, gas concentration, and/or temperature, etc. The skilled artisan will readily appreciate that appropriate adjustments can optimize indicator production for specific or desired uses.

The respective biocompatible compositions and/or surface layers have a uniform thickness, in some embodiments, when applied to a device or as a component of the device. In addition, the respective compositions layers may be formed of the same or different materials. In suitable embodiments, it is preferred that the respective compositions and/or surface layers be formed of the same material with the same thickness. In such configuration, a temperature, pressure and/or water stress, e.g., an exposure, may be uniformly applied on part or all surfaces of the device substrate. In some embodiments, one or more layers of the biocompatible compositions are applied to a device or instruments to form the indicator region.

In illustrative embodiments, the biocompatible composition is formulated such that after the biocompatible composition is applied to a proximal end of a device, i.e., constituting the indicator region, the superabsorbent polymer (SAP) is sterically arrange throughout the indicator region to ensure that water, when present, is able to contact—and accordingly swell—the SAP, i.e., the water is accessible to the SAP for adsorption via SAP surface exposure. Likewise, in some embodiments of the present invention, the SAP molecules are contiguously conformed or are arranged in a substantially contiguous configuration within the biocompatible composition, and consequently throughout the indicator region, such that water, when present, is able to continuously percolate the indicator region until the SAP swelling capacity is achieved.

Certain embodiments of the present invention include methods of applying the biocompatible compositions of the indicator material as a coating or dip coating by using a slurry or suspension of the desired fillers, binders, additive and/or solvents. The steps of the method entail, in some embodiments, preparing a solution or suspension consisting essentially of a coating component, where the coating component consists essentially of the biocompatible composition constituents, which yield acceptable results. In suitable embodiments, the medical device has a proximal end and a distal end, and where the at least one indicator region is positioned at or about the proximal end of the medical device. In suitable embodiments, the proximal end of the device and/or the indicator region is sufficiently located, configured, arranged and/or positioned on, or with respect to, the medical device such that the indicator region and/or proximal end of the device is not subjected to an exposure until after the single procedure.

In this particular embodiment, the resulting slurry is poured into the dip-coating container and a desired region of a surgical or medical device, e.g., the proximal region, is subsequently submerged into the slurry via a dip-coater or appropriate, e.g., Instron apparatus (dipping step), in illustrative embodiments. At a withdrawal rate of, for example only, 0.0762 cm/s, the coated device or region is removed from the slurry and allowed to air dry before subjecting the coated region to a drying step, in suitable embodiments. The coated region is then allowed to cool and additional coatings may be added by repeating the dipping and drying steps in various embodiments.

In accord with its application, after applied to the device or instrument at the proximal end and stabilizes, in illustrative embodiments, the biocompatible composition is now effectively the indicator region as described herein. As such, the indicator region, prior to any exposure, is present in the unmodified state. In this regard, such a device or instrument having or harboring an unmodified indicator region, has not been discharged to the extent that an affirmative discharge status requires first (i) a single-use, and (ii) a water, e.g., steam sterilization, exposure to transition the unmodified state to the modified state. Nevertheless, the indicator region possesses the ability, in some embodiments, to transition from the unmodified state to the modified state after an exposure. In suitable embodiments, the exposure comprises subjecting the medical device including the at least one indicator region to one or more autoclave cycles.

In illustrative embodiments, the exposure entails subjecting the medical device including the at least one indicator region to the presence of water, where in certain embodiments, the water presence occurs via one or more autoclave steam sterilization cycles. In suitable embodiments, the one or more steam sterilization cycles are performed for a duration at temperatures and pressures sufficient to (i) transition the at least one indicator region from the unmodified state to the modified state, and (ii) sterilize the device, as previously discussed. With respect to the indicator region per se, the transition to the modified state is readily apparent, visually and/or in a tactile manner, to an observer due to the dramatic increase in volume, e.g., via hydration, swelling or attaining its swelling capacity, of the superabsorbent polymer material as discussed above.

Similarly, another aspect of the present disclosure provides a method for determining the discharge status of a single procedure device, including (a) providing the device, where the device includes at least one indicator region configured to transition from an unmodified state to a modified state in response to an exposure, (b) subjecting the device to the exposure after the single procedure has been performed using the device, (c) assessing the transition state of the at least one indicator region, where the modified state of the at least one indicator region irreversibly identifies that the device has been subjected to the exposure after the single procedure, and (d) determining the discharge status of the device based on the transition state assessment of the at least one indicator region, where the device is affirmatively discharged when the at least one indicator region is in the modified state.

Certain embodiments, moreover, entail an irreversible identification with respect to the transition of the indicator region to the modified state, where the irreversible identification is a visual and tactile identification. In some embodiments, the modified state of the at least one indicator region renders the device clinically impractical for reuse due to the morphological consistency of the indicator region when in the modified state. In certain embodiments the one or more superabsorbent polymers is sodium polyacrylate, where the sodium polyacrylate possesses a degree of ionization ranging from about 30-100 percent. In some embodiments, the at least one indicator region includes a biocompatible composition entailing one or more of (i) at least one filler, (ii) one or more binders, (iii) one or more additives, and (iv) a solvent, and combinations thereof.

In illustrative embodiments, the methods further entail one or more of (e) labelling the affirmatively discharged device as end-of-use, (f) segregating the affirmatively discharged device from other single procedure devices that have not been affirmatively discharged, and/or (e) disposing of the affirmatively discharged device. In some embodiments, the exposure comprises subjecting the device including the at least one indicator region to a water treatment, e.g., but not limited to, one or more steam sterilization cycles. In suitable embodiments, the one or more steam sterilization cycles are performed for a duration at temperatures and pressures sufficient to (i) transition the at least indicator region from the unmodified state to the modified state, and (ii) sterilize the device.

The biocompatible composition of the indicator, in illustrative embodiments, consists of sodium polyacrylate as a non-limiting filler in a system, method or composition entailing a binder selected from alkyds, acrylic, vinyl-acrylics, polyurethanes, polyesters, melamine, epoxy, silanes, siloxanes and/or oils. In some embodiments where a solvent is employed, xylene, toluene, an alcohols or a ketones is selected in addition to or as an alternative to one or more additives, such as, but not limited to clays, kaolin, kaolinite, halloysite, diaspore, bentonite (Fuller's earth), ball clay, common clay, shale, fire clay, illite, chlorite, smectite minerals, quartz, limestone, silicate compounds, and quartz, and/or combinations thereof, to improve the mechanical properties and/or stabilize the compositions of the present invention.

When sodium polyacrylate is selected as the superabsorbent polymer, the weight percentage in biocompatible composition of the indicator is from about 30-90 percent. Along the same lines, when the binder is selected from an alkyd, acrylic, vinyl-acrylics, polyurethanes, polyesters, melamine, epoxy, silanes, siloxanes and/or oils, weight percentage in biocompatible composition of the indicator is from about 10-70 percent. Solvents such as xylene, toluene, an alcohol or a ketone, when used in the methods, systems and compositions herein, are present at a weight percentage in biocompatible composition of the indicator is from about 0.0001-99 percent. Likewise, when the indicator materials and compositions contain an additive such as clays, kaolin, kaolinite, halloysite, diaspore, bentonite (Fuller's earth), ball clay, common clay, shale, fire clay, illite, chlorite, smectite minerals, quartz, limestone, silicate compounds, and quartz, the weight percentage in the biocompatible composition of the indicator is from about 0.0001-99 percent to from about 0.1-10 percent.

Some or all of the foregoing ranges were assessed and found to be exemplary by empirical determination, while some or all of the foregoing ranges relate to the chemical or physical constraints of the composition constituents. For example, in one embodiment, a lower range as detailed above may relate to the particle size of the filler, e.g., sodium polyacrylate, binder, additives, solvents, etc. The upper limit in this context relates to, in some embodiments, the hydrated or swollen sodium polyacrylate in addition to or alternative with the binder, solvent and additive, where sizes greater than the disclosed ranges above may aggregate, precipitate out of solution and/or disengage from the device. In some embodiments, the range of ionization for sodium polyacrylate is about from 30-100%.

Figure 2:
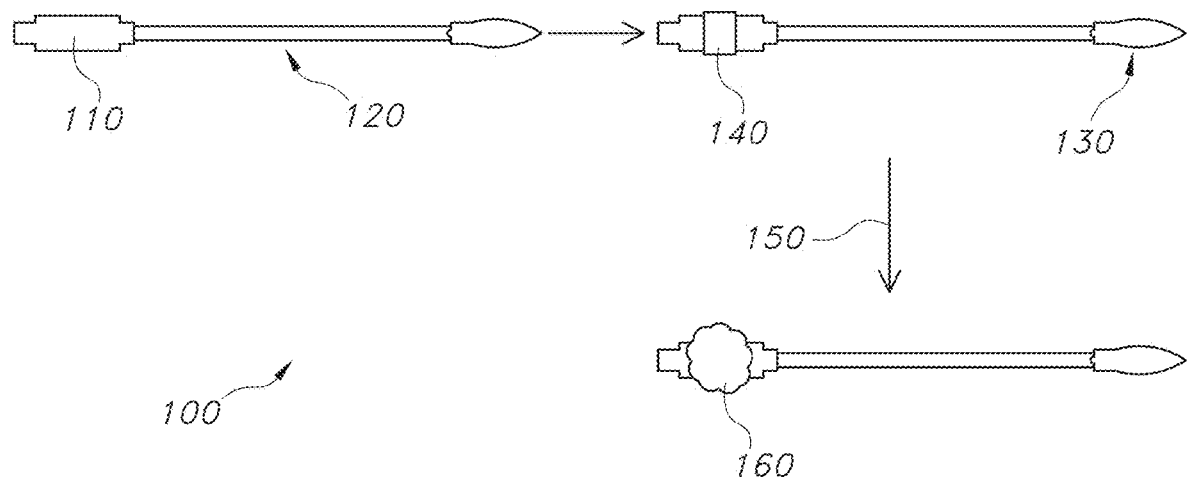
FIG. 2 is a schematic representation of a single-use superabsorbent polymer indicator on a single procedure device prior to and following steam sterilization.

FIG. 2 shows an illustrative embodiment of the present invention. In an operation 100, a medical device composed of plastic proximal end 110, conduit region 120, and distal end 130 is provided. In operation 100, plastic proximal end 110 is coated with an unmodified indicator 140 and exposed to water, which, in the present operation, is a steam sterilization procedure 150. In operation 100, steam sterilization procedure 150 transforms unmodified indicator 140 to the modified indicator 160.

EXAMPLES

The present compositions and methods will be understood more readily by reference to the following examples, which are provided by way of illustration and are not intended to be limiting in any way.

Example 1

Preparation Polymer Matrices

Superabsorbent polymer matrices. The superabsorbent polymer matrices were prepared by mixing sodium polyacrylate with one or more alkyds, acrylics, vinyl-acrylics, polyurethanes, polyesters, melamine, epoxy, silanes, siloxanes and oils, as the binding agent. Separate examples included one or more additives, e.g., clay (kaolin), limestone and quartz, to structurally stabilize the mixture, where an appropriate solvent, such as, xylene, toluene, an alcohol, or ketones were also employed in other examples.

The respective compositions, by weight percentage in the mixture, of the sodium polyacrylate, at a molecular weight of 100 to 3,000 kg/mol, binder, solvent (when included), and additives (when included) were 30-90, 10-70, 0.1-60, and 0.1-10 percent. The degree of sodium polyacrylate ionization ranged from 30-100 percent in these examples. The composition was prepared by mixing together the sodium polyacrylate and binder (with additives and/or a solvent, when included) at the concentrations noted above to produce a hydrogel slurry that was accordingly applied to the proximal end of a medical device at a thickness of 100 μm to 3 mm, which respectively corresponded to the particle size of sodium polyacrylate prior to water exposure and the hydrated sodium polyacrylate that was subsequently exposed to steam sterilization and/or water.

Example 2

Mechanism of Water-Absorbing Polymers

Figure 1B:
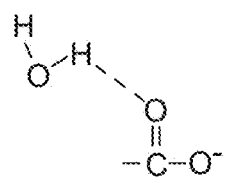

Water absorbing polymers that were used are superabsorbent macromolecules, which contain hydrophilic backbones. These polymers contain carboxylic acid and carboxylate ion groups, which indicated a favorable interaction with the water molecules. These electrostatic hydrogen bond interactions occurred between the electronegative oxygen atoms and electron deficient hydrogen atoms as shown in FIG. 1, which is an exemplary representation of such intermolecular interactions between the polymer matrix functional groups and water molecules. FIG. 1A, to this end, shows the hydrogen bonding between polymer matrix carboxylic acid groups and water molecules, while FIG. 1B depicts hydrogen bonding between the carboxylate ion group groups of the polymer matrix and water molecules. The hydrogen bonding interactions thereby decreased the energy of the system. And, moreover, while the hydrophilic polymer chains of the superabsorbent matrix have the tendency to disperse in an aqueous solution, thereby allowing for various morphological configurations—and thus increasing the entropy of the system—the polymer chains were cross-linked to form a three dimensional network. In this respect, the resulting three dimensional network structure, although allowing for swelling of the superabsorbent matrix, it precludes water molecule dissemination. Accordingly, the prepared indication compositions of this example were irreversible.

Example 3

SAPs as Sterilization Indicators

A single procedure intramedullary reamer was obtained, which consists of a plastic cylindrical component located at its proximal end, i.e., around the shaft. In this example, the plastic part (or portions of it in separate examples) was coated with sodium polyacrylate, a biocompatible superabsorbent polymer. As a result, when exposed to water, via a steam sterilization procedure, the polymer material swelled significantly and became pliable. The swelling persisted even after the device indicator region was removed from the steam environment detailed below. FIG. 2 to this end entails a schematic representation of the single-use indicator on the single procedure reamer prior to and following water exposure, e.g., via steam sterilization.

Figure 3A:
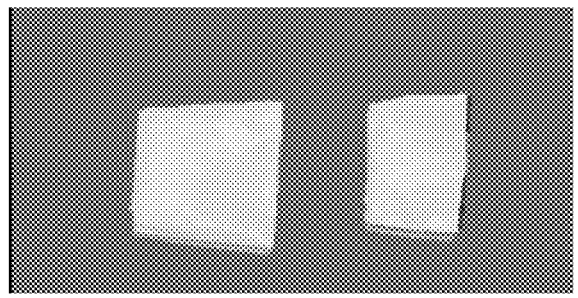
FIGS. 3A-3B are photographs of single-use superabsorbent polymer indicator pouches prior to and following steam sterilization.
Figure 3B:
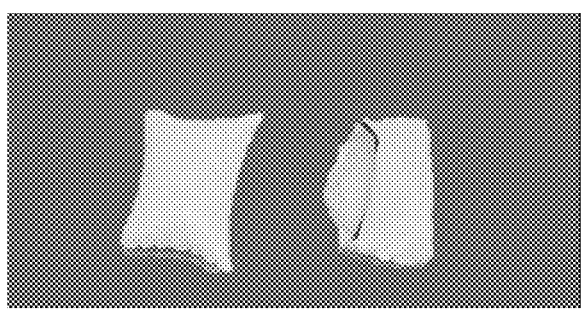

FIG. 3 further details the single-use superabsorbent polymer indicator, sodium polyacrylate, which, in this instance, was not applied to a device, in two separate pouches prior to and following steam sterilization. FIG. 3A shows the sodium polyacrylate-based indicator before being subjected to steam sterilization, while FIG. 3B is a photograph of the sodium polyacrylate-based indicator after steam sterilization. Briefly, the sodium polyacrylate compositions were placed in an open pouch of porous polypropylene, which was subsequently heat sealed to enclose the superabsorbent polymer. The two bags underwent a typical steam sterilization cycle, i.e., one gravity autoclave cycle at 274° F. for 18 minutes followed by 20 minutes of drying. As shown in the FIG. 3 photographs, the pouches before and after steam sterilization were respectively in an unmodified and modified state. The superabsorbent sodium polyacrylate polymer inside the pouch swelled to a significant extent and the swelling was retained after the procedure.

Figure 4A:
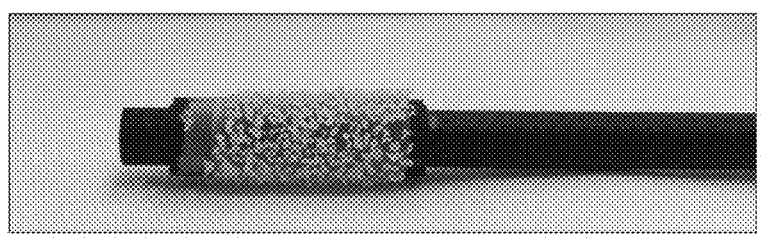
FIGS. 4A-4B are photographs of single-use superabsorbent polymers coated on the proximal end of a medical device prior to and following water exposure.
Figure 4B:
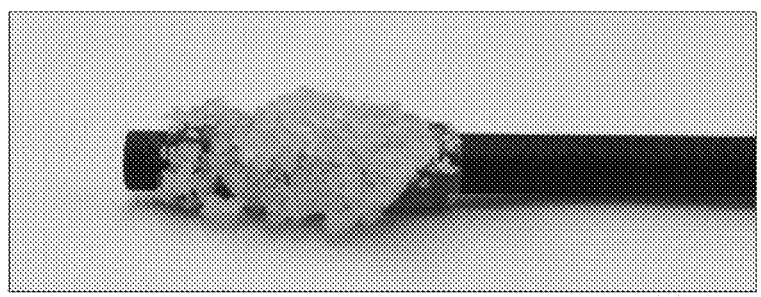

FIG. 4 further details the single-use sodium polyacrylate polymers coated on the proximal end of a medical device reamer prior to and following water exposure. FIG. 4A shows the coated sodium polyacrylate indicator before water exposure, where FIG. 4B is a photograph of the coated sodium polyacrylate indicator after such exposure. Here, the sodium polyacrylate composition was coated on a reamer shaft with an adhesive. Upon water exposure, the coated sodium polyacrylate composition indicator was swelled significantly to a soft, pliable, consistency. The results shown in FIG. 3 and FIG. 4 clearly demonstrate the utility of superabsorbent polymers as indicators for steam sterilization.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 polymers refers to groups having 1, 2, or 3 polymers. Similarly, a group having 1-5 polymers refers to groups having 1, 2, 3, 4, or 5 polymers, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference herein in their entireties and for all purposes to the same extent as if each individual publication, patent, or patent application was specifically and individually incorporated by reference in its entirety for all purposes.

What is claimed is:

1. A method for determining the discharge status of a single procedure device, comprising:
    (a) providing the device, wherein the device includes at least one indicator region configured to transition from an unmodified state to a modified state in response to an exposure wherein said indicator region comprises a biocompatible composition including one or more superabsorbent polymers possessing a swelling capacity range of about 30-500 fold the volume of the one or more superabsorbent polymers prior to being subject to exposure;
    (b) subjecting the device to the exposure after the single procedure has been performed using the device;
    (c) assessing the transition state of the at least one indicator region, wherein the modified state of the at least one indicator region irreversibly identifies by swelling of said one or more superabsorbent polymers that the device has been subjected to the exposure after the single procedure; and
    (d) determining the discharge status of the device based on the transition state assessment of the at least one indicator region, wherein the device is affirmatively discharged when the at least one indicator region is in the modified state.

2. The method of claim 1, further comprising one or more of:
    (a) labelling the affirmatively discharged device as end of-use;
    (b) segregating the affirmatively discharged device from other single procedure devices that have not been affirmatively discharged; and
    (c) disposing of the affirmatively discharged device.

3. The method of claim 1, wherein the exposure comprises the device including the at least one indicator region to (i) the presence of water, or (ii) one or more steam sterilization cycles, or both.

4. The method of claim 1, wherein the device is a single-use medical device comprising a proximal end and a distal end, and wherein the at least one indicator region is located at or about the proximal end of the medical device.

5. The method of claim 1, wherein the biocompatible composition further comprises one or more binders, one or more additives, and a solvent, and combinations thereof.

6. The method of claim 5, wherein the one or more superabsorbent polymer is present at a range of about 30-90 by weight percentage in the biocompatible composition.

7. The method of claim 6, wherein the one or more superabsorbent polymers are selected from the group consisting of polyacrylates, polyacrylamides, polyacrylamide copolymers, polyacrylic acid, sodium polyacrylate, potassium polyacrylate, lithium polyacrylate, ammonium polyacrylate, ethylene maleic anhydride copolymer, carboxymethylcellulose, polyvinyl alcohol copolymers, polyethyleneoxide, and copolymers of polyacrylonitrile, and combinations thereof.

8. The method of claim 7, wherein the one or more superabsorbent polymers is sodium polyacrylate, and wherein the sodium polyacrylate possesses a degree of ionization ranging from about 30-100 percent.

9. The method of claim 5, wherein the one or more binders are present at a range of about 10-70 by weight percentage in the biocompatible composition, and wherein the one or more binders are selected from the group consisting of alkyds, acrylics, vinyl-acrylics, polyurethanes, polyesters, melamine, epoxies, silanes, siloxanes, and oils, and combinations thereof.

10. The method of claim 5, wherein the one or more additives are present at a range of about 0.1-10 by weight percentage in the biocompatible composition, and wherein the one or more additives are selected from the group consisting of clays, kaolin, limestone, silicate compounds, and quartz, and combinations thereof.

11. The method of claim 5, herein the one or more solvents are present at a range of about 0.1-60 by weight percentage in the biocompatible composition, and wherein the one or more solvents are selected from the group consisting of xylene, toluene, alcohols, and ketones, and combinations thereof.

* * * * *